United States Patent [19]

Bruns et al.

[11] 4,146,506
[45] Mar. 27, 1979

[54] PERFUME COMPOSITIONS WITH 4-ISOPROPYL-5,5-DIMETHYL-1,3-DIOXANE

[75] Inventors: Klaus Bruns, Krefeld-Traar; Jens Conrad, Hilden; Peter Meins, Mettmann; Hinrich Möller, Düsseldorf-Benrath; Harald Schnegelberger, Leichlingen, all of Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 844,281

[22] Filed: Oct. 21, 1977

[30] Foreign Application Priority Data

Oct. 23, 1976 [DE] Fed. Rep. of Germany ....... 2648109

[51] Int. Cl.$^2$ .......................... C11B 9/00; A61K 7/46
[52] U.S. Cl. ................................. 252/522; 260/340.7
[58] Field of Search .......................................... 252/522

[56] References Cited

U.S. PATENT DOCUMENTS

| | | | |
|---|---|---|---|
| 2,769,014 | 10/1956 | Beets | 252/522 |
| 3,326,746 | 6/1967 | Cahn et al. | 252/522 |
| 3,423,430 | 1/1969 | Cahn et al. | 252/522 |
| 3,801,600 | 4/1974 | Naegli | 252/522 |
| 3,840,559 | 10/1974 | Hoffmann | 252/522 |
| 3,884,841 | 5/1975 | Maesseu et al. | 252/522 |

Primary Examiner—Veronica O'Keefe
Attorney, Agent, or Firm—Hammond & Littell

[57] ABSTRACT

A perfumery composition consisting essentially of from 1% to 50% by weight of a 4-isopropyl-5,5-dimethyl-1,3-dioxane of the formula

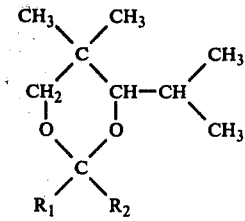

wherein $R_1$ and $R_2$ are individually members selected from the group consisting of hydrogen, alkyl having from 1 to 3 carbon atoms and cyclopropyl, and the remainder customary constituents of perfumery compositions; as well as novel 4-isopropyl-5,5-dimethyl-1,3-dioxanes of the above formula wherein both $R_1$ and $R_2$ are not simultaneously hydrogen.

7 Claims, No Drawings

4,146,506

PERFUME COMPOSITIONS WITH 4-ISOPROPYL-5,5-DIMETHYL-1,3-DIOXANE

BACKGROUND OF THE INVENTION

The present invention relates to perfumery compositions containing 4-isopropyl-5,5-dimethyl-1,3-dioxanes and the novel 2-substituted-4-isopropyl-5,5-dimethyl-1,3-dioxanes.

The use of alkylated 1,3-dioxanes as perfumes is already known from British Patent Specification 981,285, relating to compounds of the general formula

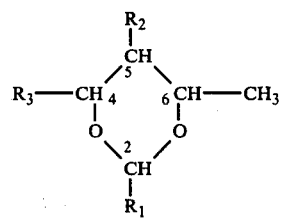

in which $R_1$ represents an alkyl radical having 4 to 9 carbon atoms, $R_2$ represents hydrogen or an alkyl radical having 1 to 4 carbon atoms, and $R_3$ represents hydrogen or a methyl radical. According to Patent Specification No. 981,285, it is essential to observe the following conditions in order to obtain usable perfumes: (1) The number of carbon atoms of the straight- or branched-chain alkyl radical $R_1$ located in the 2 position must be at least 4 but no more than 9, (2) The substituent in the 4 position must only be a methyl radical, and (3) Each ring carbon atom must carry at least one hydrogen atom. By virtue of these conditions of the said Patent Specification which greatly limit the breadth of the generic formula, it was not to be anticipated that compounds, having other than the structure initially specified, would possess perfume qualities.

Copending, commonly-assigned U.S. patent application Ser. No. 806,616, filed June 15, 1977, relates to the use of alkyl-substituted 1,4-dioxanes for use in perfumery compositions of the formula

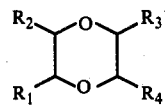

Here again, each ring carbon must carry at least one hydrogen atom, and, of course, the compound is a 1,4-dioxane.

OBJECTS OF THE INVENTION

An object of the present invention is the development of a perfumery composition with characteristic fragrances ranging from fruity, herbal to woody.

A further object of the present invention is the development of a perfumery composition consisting essentially of from 1% to 50% by weight of a 4-isopropyl-5,5-dimethyl-1,3-dioxane of the formula

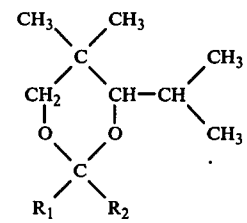

wherein $R_1$ and $R_2$ are individually members selected from the group consisting of hydrogen, alkyl having from 1 to 3 carbon atoms and cyclopropyl, and the remainder customary constituents of perfumery compositions.

A yet further object of the present invention is the obtaining of a 4-isopropyl-5,5-dimethyl-1,3-dioxane of the formula

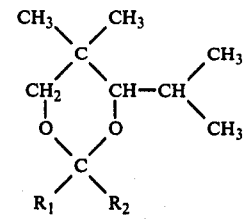

wherein $R_1$ and $R_2$ are individually members selected from the group consisting of hydrogen, alkyl having from 1 to 3 carbon atoms and cyclopropyl, with the proviso that $R_1$ and $R_2$ are not both hydrogen.

These and other objects of the present invention will become more apparent as the description thereof proceeds.

DESCRIPTION OF THE INVENTION

We have now found that 4-isopropyl-5,5-dimethyl-1,3-dioxanes of the following general formula I can be used in an advantageous manner as perfumes having a wide variety of fragrances:

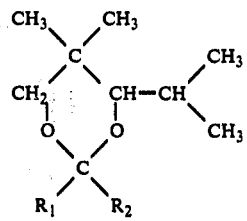

I in which $R_1$ and/or $R_2$ represent hydrogen or an alkyl or cycloalkyl radical having 1 to 3 carbon atoms.

More particularly, the invention relates to a perfumery composition consisting essentially of from 1% to 50% by weight of a 4-isopropyl-5,5-dimethyl-1,3-dioxane of the formula

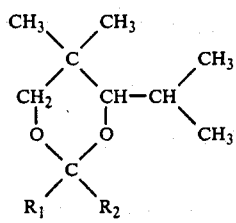

wherein R₁ and R₂ are individually members selected from the group consisting of hydrogen, alkyl having from 1 to 3 carbon atoms and cyclopropyl, and the remainder customary constituents of perfumery compositions.

Some of the 2-substituted-4-isopropyl-5,5-dimethyl-1,3-dioxanes are novel products. These are particularly 4-isopropyl-5,5-dimethyl-1,3-dioxanes of the formula

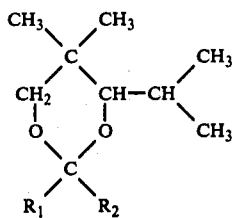

wherein R₁ and R₂ are individually members selected from the group consisting of hydrogen, alkyl having from 1 to 3 carbon atoms and cyclopropyl, with the proviso that R₁ and R₂ are not both hydrogen.

The use of the above 4-isopropyl-5,5-dimethyl-1,3-dioxanes in perfumery was completely unexpected in view of the teachings of British Pat. No. 981,285 as discussed above. The compounds of the present invention have one or two ring carbons without hydrogen atoms. The substituent in the 4 position is isopropyl and the substituents R₁ and/or R₂ must have 3 or less carbon atoms. Any supposition that the compounds of formula I would have any use in perfumery was further invalidated by virtue of the fact that 2-alkyl substituted compounds of formula I, in which at least one of the radicals R₁, R₂ had more than 3 carbon atoms, such as 2-ethyl-2-butyl-4-isopropyl-5,5-dimethyl-1,3-dioxane or 2,2-dibutyl-4-isopropyl-5,5-dimethyl-1,3-dioxane, were not suitable for perfumes, although they fulfilled the requirements of the British Patent Specification for a substituent having 4 to 9 carbon atoms in the 2 position.

The 4-isopropyl-5,5-dimethyl-1,3-dioxanes of the structure specified, and which, in accordance with the invention, are to be used as perfumes, are produced by conventional methods of organic chemistry by acetalization or ketalization of 2,2,4-trimethylpentanediol-(1,3) with aliphatic aldehydes or ketones in the presence of an acidic catalyst, respectively, according to the reaction diagram:

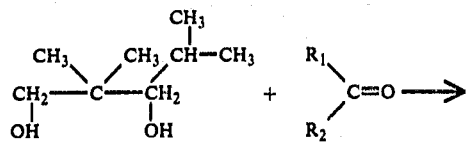

-continued

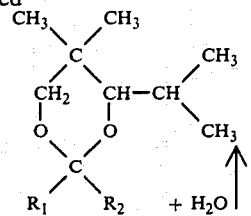

where R₁ and R₂ have the above-assigned values.

Thus, for example, Baltz et al have described the compound 4-isopropyl-5,5-dimethyl-1,3-dioxane in the "Journal für praktische Chemie" 29: 250–258 (1965), without recognizing its perfume character or mentioning its possibilities of use.

More particularly, the invention also relates to a process for the production of a 4-isopropyl-5,5-dimethyl-1,3-dioxane of the formula $$\begin{array}{c}CH_3\\\diagdown\\C\diagup CH_3\\\diagup\quad\diagdown\\CH_2\quad CH-CH\diagup CH_3\\\mid\quad\mid\quad\diagdown CH_3\\O\quad O\\\diagdown\diagup\\C\\\diagup\diagdown\\R_1\quad R_2\end{array}$$

wherein R₁ and R₂ are individually members selected from the group consisting of hydrogen, alkyl having from 1 to 3 carbon atoms and cyclopropyl, with the proviso that R₁ and R₂ are not both hydrogen, which consists essentially of the step of reacting 2,2,4-trimethylpentanediol-(1,3) with a compound of the formula $$R_1-\overset{O}{\underset{\|}{C}}-R_2$$

wherein R₁ and R₂ have the above-assigned values under ketalization conditions in the presence of an acidic catalyst, and recovering said 4-isopropyl-5,5-dimethyl-1,3-dioxane.

4-isopropyl-5,5-dimethyl-1,3-dioxanes to be used in accordance with the invention are, for example, 4-isopropyl-5,5-dimethyl-1,3-dioxane, 4-isopropyl-2,5,5-trimethyl-1,3-dioxane, 2-ethyl-4-isopropyl-5,5-dimethyl-1,3-dioxane, 2,4-diisopropyl-5,5-dimethyl-1,3-dioxane, 4-isopropyl-2,2,5,5-tetramethyl-1,3-dioxane, 2-ethyl-4-isopropyl-2,5,5-trimethyl-1,3-dioxane, 2,2-diethyl-4-isopropyl-5,5-dimethyl-1,3-dioxane, 2-cyclopropyl-4-isopropyl-2,5,5-trimethyl-1,3-dioxane, 2,4-diisopropyl-2,5,5-trimethyl-1,3-dioxane, 2,2,4-triisopropyl-5,5-dimethyl-1,3-dioxane, and 2-cyclopropyl-4-isopropyl-5,5-dimethyl-1,3-dioxane. Moreover, the 2-substituted products constitute new compounds.

The 4-isopropyl-5,5-dimethyl-1,3-dioxanes to be used in accordance with the invention are valuable perfumes having characteristic fragrances ranging from fruity, herbal to woody. A particular advantage of the perfumes in accordance with the invention is that they are capable of being combined very satisfactorily to form novel fragrances in the perfumery compositions of the invention.

The 4-isopropyl-5,5-dimethyl-1,3-dioxanes to be used, in accordance with the invention, as perfumes, can be mixed with other perfumes in a wide range of quantity ratios to form novel perfumery compositions. In general, the proportion of the 4-isopropyl-5,5-dimethyl-1,3-dioxanes to be used in the perfumery compositions according to the invention will vary from 1% to 50% by weight relative to the total perfumery composition. The remainder of the composition is conventional perfumery constituents. Such compositions can act directly as a perfume or, alternatively, can be used to perfume cosmetics such as creams, lotions, toilet waters, aerosols, toilet soaps, etc. However, as is possible with the 4-isopropyl-5,5-dimethyl-1,3-dioxanes themselves, they can also be used to improve the odor of technical products such as washing and cleaning agents, disinfectants, agents for treating textiles etc.

The following Examples are intended to further explain the subject of the invention, but without any implied limitation to these Examples.

EXAMPLES

The method for the production of representative 4-isopropyl-5,5-dimethyl-1,3-dioxanes will be given first by two procedures. The remaining products are made comparably.

Production of 4-isopropyl-5,5-dimethyl-1,3-dioxane (Example 1)

146 gm (1 mol) of 2,2,4-trimethylpentanediol-(1,3), 33 gm (1.1 mol) of paraformaldehyde, 60 ml of ethylenechloride and 0.1 ml of concentrated sulfuric acid were heated in a reactor connected to a water separator until no further water was recovered azeotropically, which took approximately 2 hours. 1.5 gm of sodium carbonate was then added to the mixture and the major quantity of the ethylenechloride was distilled off at normal pressure (sump temperature up to 155° C.). The residue remaining was subsequently fractionally distilled under vacuum. 150 gm of 4-isopropyl-5,5-dimethyl-1,3-dioxane having a b.p.$_{20}$=71° C. were obtained, corresponding to a yield of 95% of theory.

Production of 4-isopropyl-2,2,5,5-tetramethyl-1,3-dioxane (Example 5)

292 gm (2 mol) of 2,2,4-trimethylpentanediol-(1,3), 108 gm (2.02 mol) of acetone, 296 gm (2 mol) of orthoformic acid triethylester and 0.4 gm of p-toluene sulfonic acid were agitated for 1 hour at room temperature. Formic acid ester and ethanol were subsequently distilled off at normal pressure (sump temperature up to 130° C.). The residue was mixed with ether. Sodium carbonate was added to the solution and the product was washed neutral with water. The solvent was evaporated, and the residue was fractionally distilled under vacuum. 280 gm of 4-isopropyl-2,2,5,5-tetramethyl-1,3-dioxane having a b.p.$_{13}$ of 70° C. were obtained, corresponding to a yield of 70% of theory.

The other 4-isopropyl-5,5-dimethyl-1,3-dioxane, whose odor characteristics and physical data are given in the following Table, were obtained in an analogous manner.

TABLE

| Example | Designation | Boiling point °C. | Pressure Torr | $n_D$ | Odor |
|---|---|---|---|---|---|
| 1 | 4-isopropyl-5,5-dimethyl-1,3-dioxane | 71 | 20 | 1.4390 | Herbal, odor of borneol, camphor |
| 2 | 4-isopropyl-2,5,5-trimethyl-1,3-dioxane | 55 | 5.0 | 1.4306 | Minty, odor of camphor, menthol |
| 3 | 2-ethyl-4-isopropyl-5,5-dimethyl-1,3-dioxane | 32 | 0.05 | 1.4325 | Sweet, woody, fruity, sassafras, aniseed cedramber fragrance |
| 4 | 2,4-diisopropyl-5,5-dimethyl-1,3-dioxane | 94 | 20 | 1.4335 | Spicy, woody, fruity |
| 5 | 4-isopropyl-2,2,5,5-tetramethyl-1,3-dioxane | 70 | 13 | 1.4305 | Fragrance of freshly sawn wood |
| 6 | 2-ethyl-4-isopropyl-2,5,5-trimethyl-1,3-dioxane | 70 | 4.0 | 1.4375 | Minty, leathery, oryclon fragrance |
| 7 | 2,2-diethyl-4-isopropyl-5,5-dimethyl-1,3-dioxane | 103 | 17 | 1.4420 | Nutty, lovage, plum-jam fragrance |
| 8 | 2-cyclopropyl-4-isopropyl-2,5,5-trimethyl-1,3-dioxane | 98 | 3.0 | 1.4508 | Jasmone fragrance |

All the compounds given in the above Examples have the described fragrances which render them suitable for producing a wide variety of perfumery compositions. Such compositions can be used to perfume a wide variety of products such as cosmetics, washing agents, soaps as well as technical products in concentrations of approximately 0.05% to 2% by weight. Examples of perfumery compositions having a content of the 4-isopropyl-5,5-dimethyl-1,3-dioxanes in accordance with the invention are given hereinafter.

EXAMPLE 9

Fantasy Lavender

| | |
|---|---|
| 4-isopropyl-5,5-dimethyl-1,3-dioxane Example 1 | 500 parts by weight |
| Terpineol | 100 parts by weight |
| Lavendine oil Abrialis | 100 parts by weight |
| Linalyl acetate | 100 parts by weight |
| Linalool | 50 parts by weight |
| Ketone Musk | 40 parts by weight |
| Lavender oil | 30 parts by weight |
| Cumarin | 20 parts by weight |
| Sandalwood manufactured by the Firm Haarmann & Reimer | 20 parts by weight |
| Patchouli oil Sing. | 20 parts by weight |
| Camphor | 15 parts by weight |
| Ambroxan, 10% in isopropyl myristate | parts by weight |
| | 1000 parts by weight |

EXAMPLE 10

Conifer composition

| | |
|---|---|
| 4-isopropyl-2,2,5,5-tetramethyl-1,3-dioxane, Example 5 | 500 parts by weight |
| Pine needle oil, Siberian | 200 parts by weight |
| Dwarf-pine oil | 100 parts by weight |
| Bergamot oil | 50 parts by weight |
| Lavandine oil | 50 parts by weight |
| Cypress oil | 20 parts by weight |
| Eucalyptus oil | 20 parts by weight |
| Cedryl acetate | 20 parts by weight |
| Hydroxycitronellal-dimethylacetal | 20 parts by weight |
| Oak moss, absolute 50% | 10 parts by weight |
| Rosemary oil | 8 parts by weight |
| Lauric aldehyde | 1 part by weight |
| α, γ-hexanol | 1 part by weight |
| | 1000 parts by weight |

EXAMPLE 11

Fantasy Jasmine

| | |
|---|---|
| 2-cyclopropyl-4-isopropyl-2,5,5-tri-methyl-1,3-dioxane, Example 8 | 120 parts by weight |
| Benzyl acetate | 455 parts by weight |
| Phenylethyl alcohol | 220 parts by weight |
| Geraniol from citronella oil | 58 parts by weight |
| Cinnamic alcohol | 35 parts by weight |
| Cedar wood oil, Virginia | 30 parts by weight |
| Benzyl salicylate | 25 parts by weight |
| Ylang-ylang oil | 20 parts by weight |
| Methyl anthranilate | 20 parts by weight |
| Cananga oil | 10 parts by weight |
| Isoeugenol | 5 parts by weight |
| Ethyl salicylate | 2 parts by weight |
| | 1000 parts by weight |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfumery composition consisting essentially of from 1% to 50% by weight of a 4-isopropyl-5,5-dimethyl-1,3-dioxane of the formula

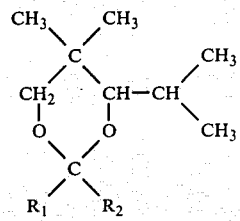

wherein $R_1$ and $R_2$ are individually members selected from the group consisting of hydrogen, alkyl having from 1 to 3 carbon atoms and cyclopropyl, and the remainder customary constituents of perfumery compositions.

2. The perfumery composition of claim 1 wherein said customary constituents of perfumery compositions include at least one other perfume.

3. The perfumery composition of claim 1 wherein $R_1$ is methyl and $R_2$ is hydrogen.

4. The perfumery composition of claim 1 wherein $R_1$ is ethyl and $R_2$ is hydrogen.

5. The perfumery composition of claim 1 wherein $R_1$ is methyl and $R_2$ is methyl.

6. The perfumery composition of claim 1 wherein $R_1$ is ethyl and $R_2$ is ethyl.

7. The perfumery composition of claim 1 wherein $R_1$ is cyclopropyl and $R_2$ is methyl.

* * * * *